US007188514B2

(12) United States Patent
Blomkvist et al.

(10) Patent No.: US 7,188,514 B2
(45) Date of Patent: Mar. 13, 2007

(54) METHOD FOR PROVIDING AN OIL CHANGE INDICATION TO AN OPERATOR OF AN INTERNAL COMBUSTION ENGINE

(75) Inventors: Gisela Blomkvist, Göteborg (SE); Arne Andersson, Mölnlycke (SE); Filip Acke, Göteborg (SE)

(73) Assignee: Ford Global Technologies, LLC, Dearborn, MI (US)

( * ) Notice: Subject to any disclaimer, the term of this patent is extended or adjusted under 35 U.S.C. 154(b) by 101 days.

(21) Appl. No.: 11/157,612

(22) Filed: Jun. 21, 2005

(65) Prior Publication Data

US 2006/0005609 A1 Jan. 12, 2006

(30) Foreign Application Priority Data

Jul. 6, 2004 (EP) .................................. 04015811

(51) Int. Cl.
*G01N 33/26* (2006.01)

(52) U.S. Cl. ..................................................... 73/53.05

(58) Field of Classification Search .................. 73/116, 73/117.2, 53.05

See application file for complete search history.

(56) References Cited

U.S. PATENT DOCUMENTS

| | | | | |
|---|---|---|---|---|
| 5,750,887 | A * | 5/1998 | Schricker | 73/117.3 |
| 6,786,080 | B2 * | 9/2004 | Jakoby et al. | 73/54.01 |
| 6,966,304 | B2 * | 11/2005 | Nagaishi et al. | 123/480 |
| 7,121,250 | B2 * | 10/2006 | Yokoyama | 123/196 R |
| 2005/0188685 | A1 * | 9/2005 | Folliot et al. | 60/286 |

FOREIGN PATENT DOCUMENTS

| | | | |
|---|---|---|---|
| EP | 1357280 | A2 * | 10/2003 |
| JP | 7098168 | | 4/1995 |

OTHER PUBLICATIONS

"An Acoustic Automotive Engine Oil Quality Sensor", Hammond et al., 1997 IEEE International Frequency Control Symposium, pp. 72-80.

SAE 2000-01-1235, "Fuel Transport to the Crankcase, Oil Dilution and HC Return with Breather Flow During the Cold Operation of a SI Engine", Shayler et al., SAE 2000 World Congress, Detroit, MI, Mar. 6-9, 2000.

SAE 2001-01-2838, "The build-Up of Oil Dilution by Gasoline and the Influence of Vehicle Usage Pattern", Shayler et al., International Fall Fuels and Lubricants Meeting and Exposition, Baltimore, MD, Oct. 16-19, 2000.

SAE 2002-01-1647, "Study of Fuel Dilution in Direct Injection and Multipoint Injection Gasoline Engines", Sagawa et al., International Fall Fuels and Lubricants Meeting and Exhibition, Reno, NV, May 6-9, 2002.

* cited by examiner

*Primary Examiner*—Hezron Williams
*Assistant Examiner*—John Fitzgerald
(74) *Attorney, Agent, or Firm*—Diana D. Brehob

(57) ABSTRACT

A method for providing an oil change indication to an operator of an internal combustion engine having an exhaust-after-treatment system requiring regeneration, The method includes detecting regeneration events performed on the exhaust-after-treatment system; detecting oil temperature events each time unit an oil temperature is over a threshold value, and providing the oil change indication to the operator as a function of the detected regeneration events and the detected oil temperature events.

15 Claims, 1 Drawing Sheet

METHOD FOR PROVIDING AN OIL CHANGE INDICATION TO AN OPERATOR OF AN INTERNAL COMBUSTION ENGINE

FIELD OF THE INVENTION

The present invention relates to a method for providing an oil change indication to an operator of an internal combustion engine and more particularly to internal combustion engine having an exhaust-after-treatment system requiring regeneration.

BACKGROUND OF INVENTION

As is known in the art, one technique used to reduce NOx emissions from a diesel engine is to use a NOx storage catalyst or NOx trap. In a NOx storage catalyst, the NOx in the exhaust is absorbed on a catalytic surface. Unfortunately, the NOx trap gets polluted (or filled) by NOx after a period of time. When it is full, the NOx trap requires regeneration to consume the NOx. Regeneration means, in this context, that the exhaust composition is altered momentarily, i.e., the engine is run “rich”, i.e., with a surplus of fuel compared to the amount of oxygen that is available for the combustion. This results in large amounts of CO in the exhausts. The CO will enter the NOx storage catalyst, and react with the trapped NOx to form CO2 and N2.

There are, however, several problems connected to the regeneration process. For example, the regeneration process can contaminate the engine oil, since a part of the diesel fuel might hit the cylinder walls prior to being ignited. Once the diesel fuel has hit the cylinder walls, it will may absorbed in the thin oil film covering the cylinder walls, and eventually end up in the engine oil sump. If the oil in the sump is hot, some of the fuel will evaporate, hence leaving the oil. The evaporated fuel will eventually enter the engine intake through the oil vapor recovery system, and take part in a subsequent combustion, but the heavier fractions of the fuel may remain in the oil until the oil is changed. The fuel dilution of the engine oil is very detrimental to the oil quality. Of course, oil changes with close intervals will solve the problems with oil dilution, but this can be a very costly method; in a worst case scenario, the oil might be severely diluted after only a couple of thousands of kilometers, in less severe driving conditions, the oil might be acceptable after more than a hundred thousand kilometers. Closely spaced oil change intervals is therefore a very blunt way of ensuring a proper oil quality; it is unnecessary to change the oil often if the driving conditions are such that only few catalyst regenerations are necessary, and the oil often will reach temperatures allowing fuel evaporation.

One major problem with the oil dilution is that it is very complex; various regeneration strategies have different dilution effects, and the evaporation of fuel from the oil is very temperature dependent.

In the prior art addressing this problem, there are different approaches to this problem; in SAE 2002-01-1647, by T. Sagawa et al, the dilution process in a direct injected gasoline engine is studied. Gasoline is however quite different from diesel fuel, especially when it comes to evaporation characteristics.

SAE 2000-01-2838 and SAE 2000-01-1235, both by P. J. Shayler et al, also describe fuel dilution of the oil in direct injected gasoline engines.

XP 010257416 (ISBN 0-7803-3728-X) describes an onboard sensor for measuring the viscosity of engine oil. This sensor measures however only the viscosity of the oil.

In a diesel engine, the viscosity will however remain quite unchanged, regardless of the fuel dilution level. Other oil characteristics like, e.g., the tribological characteristics, do however not remain the same with a diluted oil.

U.S. Pat. No. 5,169,785 describes a method for determining the fuel dilution of an oil by means of subjecting the oil for an ESR (electron spin resonance) spectrographic analysis. The method’s basic principle is to measure the presence of vanadium in different molecule structures with different electron spin resonance. At present, this is regarded as a much too complicated and expensive method for on board vehicle use.

Finally, JP-A-7 098 168 describes a device for sensing the viscosity of engine oil. This device suffers from the same shortcomings as the device according to XP 010257416, namely that it does not measure the actual fuel dilution of the oil, but rather the viscosity drop emanating from the dilution. As previously stated, this makes the device less useful for diesel engines.

Another severe problem for many engine types (mainly on diesel engines and direct injected gasoline engines) is soot emissions. One technique used to reduce the emissions of soot is by means of soot filters. The soot filter filters out soot particles in the exhausts. However, after a while, the filter is full and needs regeneration. The regeneration process for a soot filter is very similar to the regeneration process for a NOx trap. There is however one major difference; the regeneration for the soot filter does not require an oxygen free environment. On the contrary, it is advantageous with oxygen in the exhausts, since the oxygen will react with the trapped soot particles and “post-combust” them into carbon dioxide (CO2) and water (H2O). One very critical demand on the exhausts for regeneration of soot is, however, the exhaust temperature; if the temperature is too low, the soot particles will not react with the oxygen in the exhaust.

SUMMARY OF THE INVENTION

In accordance with the present invention, a method is provided for providing an oil change indication to an operator of an internal combustion engine having an exhaust after-treatment system requiring regeneration, The method includes detecting regeneration events performed on the exhaust-after-treatment system; detecting oil temperature events each time unit an oil temperature is over a threshold value, and providing the oil change indication to the operator as a function of the detected regeneration events and the detected oil temperature events.

In one embodiment, the oil change indication is provided to the operator additionally as a function of engine run time.

BRIEF DESCRIPTION OF DRAWINGS

In the following, the invention will be described with reference to the appended drawings, wherein.

DESCRIPTION OF PREFERRED EMBODIMENTS

Figure 1:
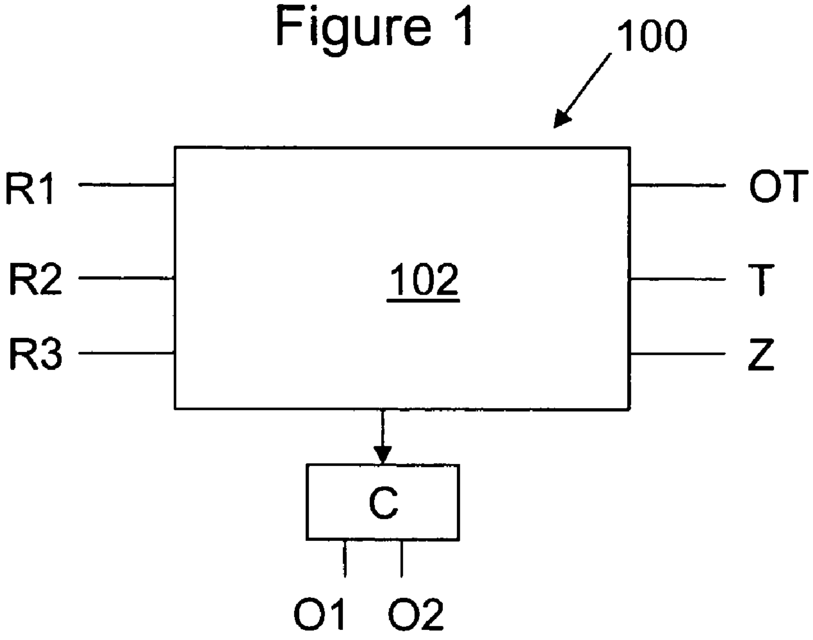
FIG. 1 is a schematic view of a counter according to the present invention.

In FIG. 1, a counter/comparator assembly 100 according to the present invention is shown. In this embodiment, the counter/comparator assembly 100 comprises a counter 102 with three increase input terminals R1, R2, R3, one zero set input terminal Z, one oil temperature input terminal OT, and one time input terminal T. The counter 102 makes calculations of an oil dilution level in a diesel or gasoline engine crankcase, in a way that will be described later. The counter 102 is connected to a comparator C, comprising at least two output terminals O1 and O2.

Figure 2:
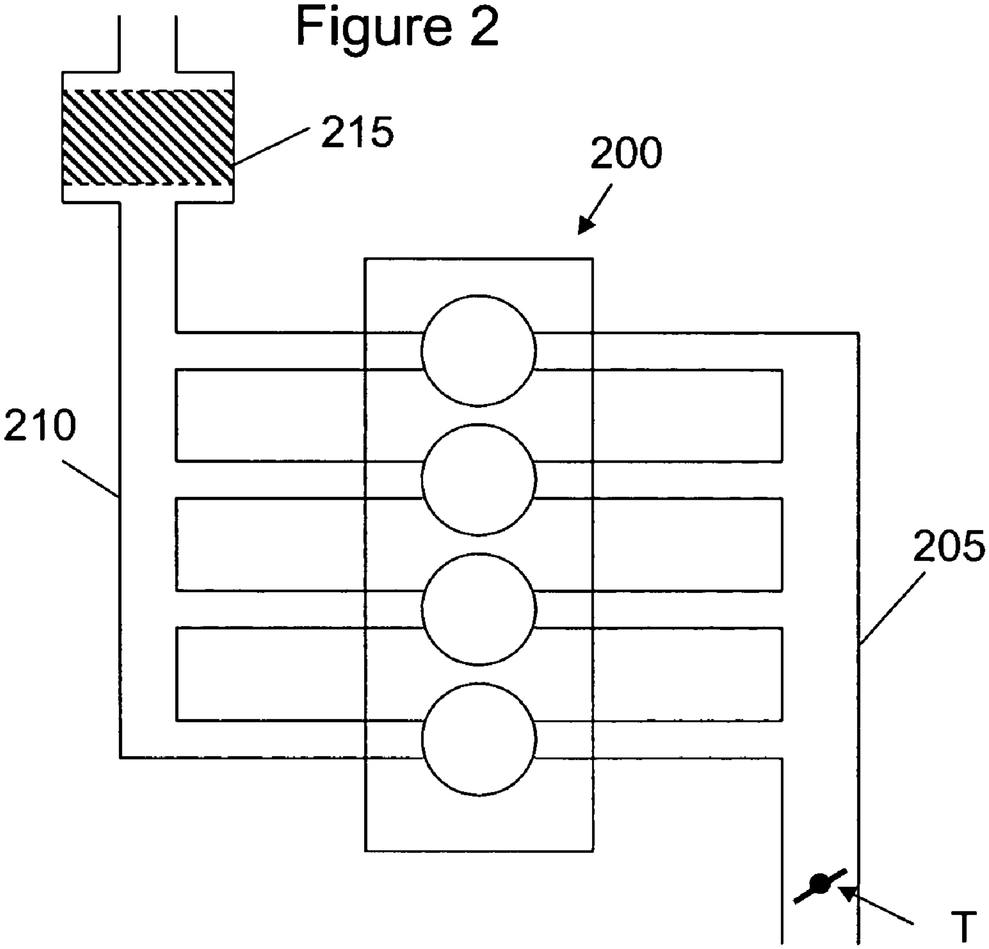
FIG. 2 is a schematic view of a diesel engine equipped with a NOx storage catalyst and the counter of FIG. 1.

FIG. 2. depicts an engine 200 fitted with an inlet plenum 205 and an exhaust plenum 210. The exhaust plenum 210 is connected to a NOx storage catalyst 215. The inlet pressure in the inlet plenum 205 can be controlled by means of a throttle T.

In the following, the function of the above components will be described.

As implied above, a regeneration process requires exhausts with low oxygen content, high temperature and presence of carbon monoxide (CO) and/or unburned hydrocarbons. For a given engine load, this can be achieved in at least two ways, namely;

1. by throttling the engine; this will decrease the amount of oxygen that is let into the cylinders, and/or
2. by injecting more fuel into the cylinders; as the fuel burns, the oxygen in the cylinder will be consumed, and the temperature of the exhaust increases.

In many cases, a combination of throttling and injection of more fuel is employed. As is well known by persons skilled in the art, injecting more fuel leads to an increased power output from the engine. This effect is partly reduced by the increased pumping work that will result if the engine is throttled, and can be further reduced by careful choice of injection timing; by using a very late injection (hereinafter referred to as LI), it is possible to achieve the desired exhaust composition with only a minor increase in engine output.

At "normal" engine operation, the engine 200 has a surplus of oxygen, i.e. there will be plenty of oxygen entering the exhaust plenum 210, and hence the NOx storage catalyst 215. Oxygen efficiently prevents conversion of NOx in any catalyst. In a NOx storage catalyst, the NOx molecules are "stored" on the catalyst surface. After some time of engine operation, the catalyst is full, and hence not be able to store more NOx. When the catalyst is full, it is regenerated. NOx storage catalysts are regenerated by being subjected to a relatively high concentration of carbon monoxide (CO) and unburned hydrocarbons (HC) at an elevated temperature. A diesel engine has, as mentioned, usually very low emissions of CO, due to the surplus of oxygen in the combustion, but for the regeneration occurs with CO and/or HC.

CO is formed when a fuel is burned with a deficiency of oxygen. In the preferred embodiment, CO is obtained by a combination of two strategies; firstly, the inlet plenum 205 throttle, T, controls the amount of oxygen that enters the cylinder. Secondly, the late injection, LI, supplies more fuel to the combustion chamber without increasing the engine output torque too much. The load increase that emanates from the late injection is partly counteracted by the pumping losses that occur due to the throttling of the intake air, as is well understood by persons skilled in the art. The amount of late injection, LI, i.e. the length of the injection pulse, differs significantly between the different load cases.

One major problem connected to regeneration by means of late injection is, as implied earlier, that the spray from the injector will penetrate far into the combustion chamber, and eventually, fuel will hit the cylinder walls. The fuel hitting the cylinder walls will be solved in the oil film covering the walls, and eventually end up in the engine sump, diluting the oil.

As mentioned earlier, some fuel fractions will evaporate from the oil when the oil temperature is high; some fuel fractions are, however, too heavy to evaporate, even at the highest allowable oil temperature.

As stated above, the dilution of the oil that results from the regeneration process decreases the life span of the oil.

FIG. 1 shows the counter 1 that is adapted to count various events that affect oil life span. Input terminal T gets an input signal as soon as the engine is running; as is the case with all engines, the oil is being used whenever the engine is running. Each time unit that the engine is running increases the counter setting. The input terminals R1, R2 and R3 receive an input signal when a regeneration process corresponding to any of the regeneration events represented by the input terminals R1, R2 and R3 occurs. An input signal on any of these input terminals increases the counter setting by a predetermined amount, which varies between the input terminals, depending on how much oil dilution that will result from the corresponding regeneration event. The counter also includes the input terminal for oil temperature, OT. The function of this input terminal is to decrease the counter setting whenever the oil temperature is above a threshold value. The amount of decrease is however strictly limited; the minimum counter setting is the sum of all counter setting increases performed by the input terminal T, and about 50% of the counter setting increases performed by the input terminals R1, R2 and R3. The reason for this is that running the engine with a high oil temperature does not prolong the life of undiluted oil. For a diesel engine, only about 50% of the fuel diluting the oil will evaporate, unless the engine operating conditions are extreme. Such extreme conditions are prolonged full load operation, e.g., on the German Autobahn. Under such conditions, the oil can be fully recovered, i.e., all fuel will evaporate from the oil.

Finally, regarding input terminals, the counter is fitted with a zero-setting input terminal Z, which sets the counter setting to zero when the oil is changed.

The counter 1 is further connected to a comparator C. The comparator C compares the counter setting with predetermined values corresponding to the values on which it is appropriate to change the oil, or inform an Engine Control Unit (ECU, not shown) that the oil soon needs an exchange. According to the described embodiment, the comparator C is equipped with two output terminals O1, O2. The output terminal 01 can be connected to the ECU of the engine 200. At a predetermined value the ECU is informed that the counter setting is approaching the predetermined value for oil exchange; in such a case, the ECU will avoid running regeneration strategies that dilutes the engine oil with more fuel than necessary. The other output terminal, O2, is connected to a signal means (not shown) in the vehicle, which signal means will inform the vehicle operator that it is time to change the oil.

There is, however, a second counter design that should be mentioned. In the above description, there is only one counter, responsible for both dilution wear and "ordinary wear", i.e., oil wear due to aging and normal engine operation. In some cases, it might, however, be preferred to use a double counter, i.e., one counter responsible for counting the "ordinary wear" and one counter for counting the "dilution wear". In such a design, each counter will have its own comparator comparing the counter setting. When either of the counters has reached a predetermined value, the comparator will signal to the operator that it is time for an oil exchange.

Further, the counter can be connected to an oil level meter; when the oil is diluted (may it be with fuel, water, or any liquid), its volume will increase. By means of an oil level meter, the oil volume can be measured. If the oil volume increases over a certain value, the operator will be informed that it is time for an oil change. Naturally, the operator will also be informed if the oil volume would decrease under a certain level.

Still further, an oil pressure meter can be used to receive information regarding the oil status; the oil pressure will be lower at a given engine speed the lower the viscosity of the oil. It is, however, difficult to establish a dilution level based on the oil viscosity. Firstly, the oil viscosity differs between different oil brands; secondly, the viscosity differs depending on oil temperature; lastly, the viscosity versus oil temperature will vary significantly depending on engine oil grade. All this combined make it very hard to establish an oil pressure setting informing the operator about when the oil is to be changed.

The above description refers to exemplary embodiments of a counter for a diesel engine requiring NOx storage catalyst regenerations. There are, however, many variants possible within the scope of the invention. For example, the number of input terminals can be varied from only one (counting only the number of regenerations), up to a plausible number of input terminals. Also, the input terminals for oil temperature, OT, and for engine running time, T, are optional, but preferred. The output terminals O1 and O2 can be limited to a single output, telling either, or both, the engine and/or vehicle operator that it is time to change the oil.

Thus, a method is provided for providing an oil change indication to an operator of an internal combustion engine having an exhaust-after-treatment system requiring regeneration. The method includes detecting regeneration events performed on the exhaust-after-treatment system; detecting oil temperature events each time unit an oil temperature is over a threshold value; and providing the oil change indication to the operator as a function of the detected regeneration events and the detected oil temperature events. In one embodiment, the oil change indication is provided to the operator additionally as a function of engine run time.

Furthermore, the counter has been described as being fitted on a diesel engine. There is, however, nothing that prevents the counter from being fitted on other internal combustion engines requiring catalyst regenerations that dilute the engine oil, e.g., direct injected gasoline engines. The scope of the invention is determined by the appended claims.

The invention claimed is:

1. A method for providing an oil change indication to an operator of an internal combustion engine having an exhaust-after-treatment system requiring regeneration, comprising:

detecting regeneration events performed on the exhaust-after-treatment system;

detecting oil temperature events each time unit an oil temperature is over a threshold value; and providing the oil change indication to the operator as a function of the detected regeneration events and the detected oil temperature events.

2. The method recited in claim 1, further comprising: providing the oil change indication to the operator as a function of engine run time.

3. The method recited in claim 1 wherein the regeneration events comprising one of: decreasing the amount of oxygen that is introduced into the cylinder of the engines and injecting additional fuel into the cylinders.

4. The method recited in claim 1 wherein the oil change interval is further a function of the type of regeneration event.

5. The method recited in claim 1 including:

zero-setting a first counter and a second counter after an oil change;

incrementing the first counter for each after-treatment system regeneration event;

incrementing the second counter for each time unit the oil temperature is over the threshold value; and providing the indication to the operator based on the values of the first and second counters.

6. The method recited in claim 1 including:

zero-setting a counter after an oil change, incrementing the counter for each after-treatment system regeneration event;

decrementing the counter for each time unit the oil temperature is over the threshold value; and providing the indication to the operator when the counter (102) has reached a predetermined level.

7. The method recited in claim 6, further comprising: increasing the counter setting for every time unit the engine is running.

8. The method recited in claim 6, further comprising operating a further counter for counting the engine run time, and signalling when said further counter has reached a predetermined level.

9. A method for providing an oil change indication to an operator of an internal combustion engine having an exhaust after treatment system requiring regeneration, comprising:

detecting regeneration events performed on the exhaust-after-treatment system; and providing the oil change indication to the operator as a function of the detected regeneration events.

10. The method of claim 9, further comprising:

detecting oil temperature; and basing the oil change indication as a function of oil temperature.

11. The method of claim 10 wherein said oil change indication is based on a duration of time at which oil temperature exceeds a threshold.

12. The method of claim 9, further comprising: basing said oil change indication on a total amount of time the engine has been operated.

13. The method of claim 10 including:

zero-setting a counter after an oil change, increasing the counter for each after-treatment system regeneration event;

decreasing the counter for each time unit the oil temperature is over the threshold; and providing the indication to the operator when the counter (102) has reached a predetermined level.

14. The method of claim 13, further comprising: limiting the decreasing of the counter.

15. The method of claim 14 wherein said limiting provides that the value in the counter is greater than zero.

* * * * *